United States Patent [19]
Inoue

[11] Patent Number: 5,117,357
[45] Date of Patent: May 26, 1992

[54] METHOD OF DEMARCATING ONE-DIMENSIONAL DISTRIBUTION

[75] Inventor: Takanobu Inoue, Hyogo, Japan

[73] Assignee: Toa Medical Electronics Co., Ltd., Kobe, Japan

[21] Appl. No.: 279,950

[22] Filed: Dec. 5, 1988

[30] Foreign Application Priority Data

Jun. 10, 1988 [JP] Japan ................ 63-142849

[51] Int. Cl.$^5$ .............................. G06F 15/42
[52] U.S. Cl. ....................... 364/413.08; 356/39
[58] Field of Search ........... 364/413.08, 413.07, 364/555; 377/6, 10, 13; 356/39; 424/3; 382/6

[56] References Cited

U.S. PATENT DOCUMENTS

| | | | |
|---|---|---|---|
| 4,007,011 | 2/1977 | Greaves et al. | 23/259 |
| 4,325,706 | 4/1982 | Gershman et al. | 436/63 |
| 4,475,236 | 10/1984 | Hoffman | 377/10 X |
| 4,706,207 | 11/1987 | Hennessy et al. | 364/555 |

FOREIGN PATENT DOCUMENTS

2034058  2/1987  Japan .................. 356/39

Primary Examiner—Jerry Smith
Assistant Examiner—David Huntley
Attorney, Agent, or Firm—Fitch, Even, Tabin & Flannery

[57] ABSTRACT

A method for demarcating a reticulocyte particle group from a red blood cell particle group in a one-dimensional frequency distribution assumes a normal distribution on one side of the distribution. Various positions $Xs_1, Xs_2, \ldots, Xs_n$, which respectively indicate frequencies that are $p_1, p_2, \ldots p_n$ percent (where n is an integer of 3 or greater) of a peak frequency of the distribution, on the normal side of the distribution, are determined. An average value and standard deviation of the normal distribution is determined from these values. A threshold value is next obtained from the average value and standard deviation, the threshold value being used to separate the reticulocyte group from the red blood cell group. The average value and standard deviation may be obtained using a least square method or by computing the mean of several average values and standard deviations.

2 Claims, 6 Drawing Sheets

METHOD OF DEMARCATING ONE-DIMENSIONAL DISTRIBUTION

BACKGROUND OF THE INVENTION

This invention relates to a method of demarcating two particle groups the boundary of which is not perfectly clear physiologically or morphologically, as is the case with mature red blood cells and reticulocytes which correspond to immature blood cells, on a plot of a one-dimensional distribution such as a particle distribution.

Immature red blood cells in a blood are referred to as reticulocytes and ordinarily make up about 0.7-2.2% of the total number of red blood cells. Measuring reticulocyte count is useful in substantiating diagnoses of acute internal bleeding, hemolytic anemia, aplastic anemia and another illnesses, in monitoring progress following the administration of medication, etc., and is thus of great importance in the field of medical examination.

In order to count reticulocytes, the conventional approach is to use a method in which a blood smear dyed with a basic dye such as new methyl blue or brilliant cresyl blue is observed and the percentage of the colored reticulocytes contained in the total number of red blood cells is determined by visual computation.

This method requires a great amount of time and labor for such pre-treatment as dying of the blood sample and for visual computation following dying and therefore is unsuitable where a large number of samples is concerned.

Figure 8:
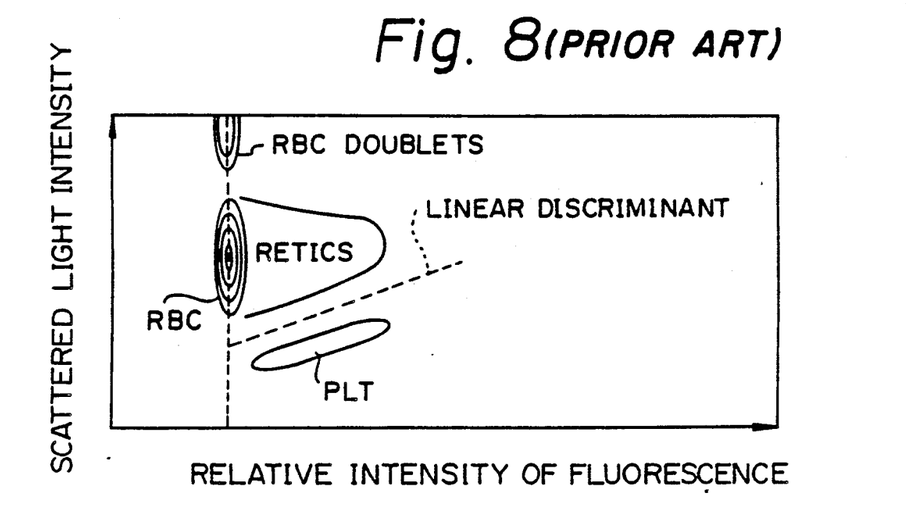
FIGS. 8, 9 and 10 are views useful in describing prior-art methods.

Accordingly, several methods of automating the counting of reticulocytes by utilizing flow cytometry have been proposed. For example, the specification of U.S. Pat. No. 4,325,706 describes a method of measuring a blood sample, which is fluorescently dyed with acridene orange, by means of a flow cytometer, and determining the reticulocyte count based on a plot of a two-dimensional distribution prepared from signals indicative of fluorescence and scattering detected from individual particles. FIG. 8 is a view of FIG. 8B of the drawings in the above-mentioned specification. The horizontal axis represents the signal strength of red fluorescence detected from the particles, and the vertical axis represents the signal strength of scattered light detected from the particles. A red blood cell (RBC) particle group and a reticulocyte (RETICS) particle group in the center of the view are demarcated from a platelet (PLT) particle group by a diagonally extending linear discriminant. Next, the platelets demarcated by the discriminant are removed, after which a one-dimensional distribution having the red fluorescense signal strength plotted along the horizontal axis is drawn regarding the remaining red blood cell particles and reticulocyte particles. The result is the one-dimensional distribution shown in FIG. 9 (which is taken from FIG. 9 of the above-mentioned specification).

Figure 9:
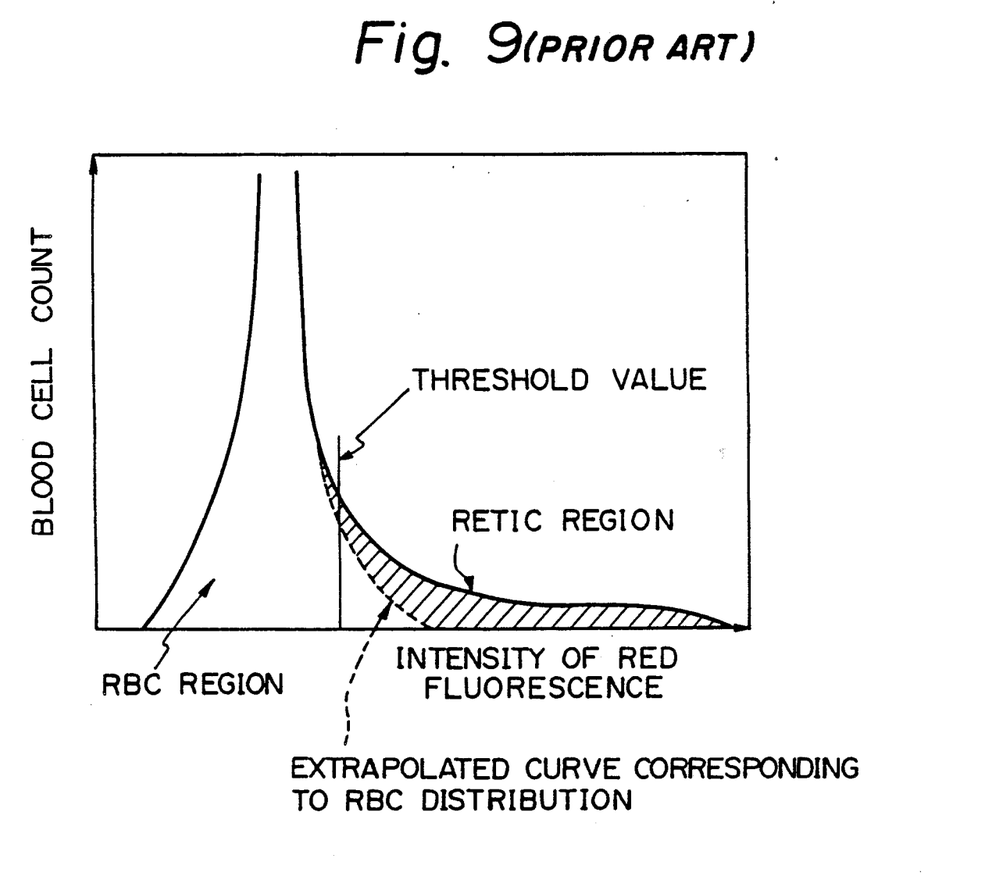

In the aforesaid U.S. patent, a normal distribution curve is estimated from the curve on the right side of the red blood cell (RBC) region in FIG. 9, and the curve on the right side of the red blood cell distribution is extrapolated (the curve indicated by the dashed line in FIG. 9). This is based on an assumption that a frequency distribution of the red blood cells conforms to a normal distribution. A point at which this extrapolated curve departs from the original frequency distribution curve is determined as a threshold value, a region having a fluorescence intensity above this threshold value and bounded by the original frequency distribution curve and the above-mentioned extrapolated curve serves as a reticulocyte (RETIC) region, the number of particles contained in this region is counted, and this number is adopted as the reticulocyte count.

Figure 10:
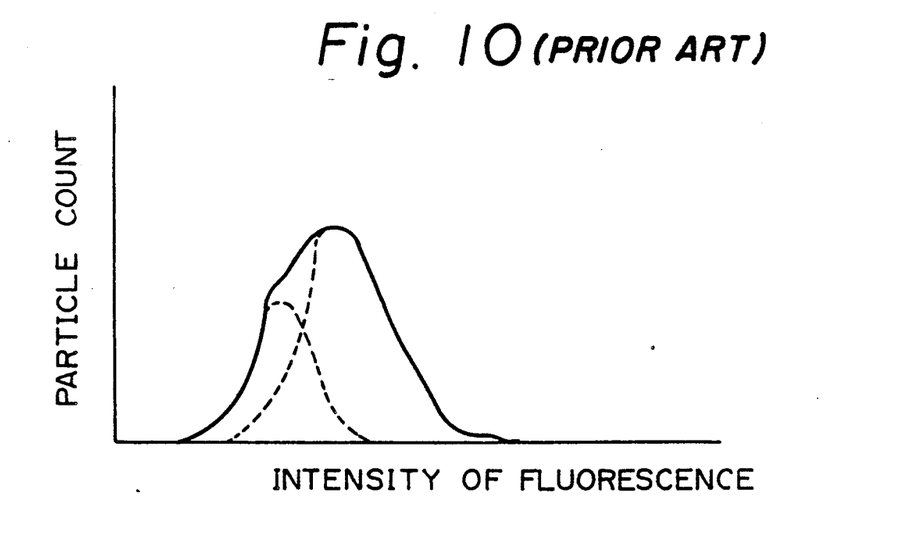

In a case where the one-dimensional frequency distribution is formed by partially superimposing a plurality of particle groups having completely different shapes, properties and origins, it is possible to estimate the distribution of each particle group and count the number of particles in each particle group. For example, the specification of Japanese Patent Application Laid-Open (KOKAI) No. 63-32347 describes, as one example, analyzing a red blood cell particle size distribution (a one-dimensional frequency distribution) of blood in which blood cells of two different sizes are mixed owing to a blood transfusion, estimating the particle size distribution of each of these two particle groups, and determining the red blood cell count in each group. FIG. 10 illustrates the particle size distribution for this case, in which the dashed lines represent the estimated distribution.

However, the relationship between red blood cells and reticulocytes within the same specimen is not a relationship between two entirely different particle groups. That is, in the course of red blood cell maturation, a reticulocyte is an immature red blood cell in a stage just prior to becoming a mature red blood cell. (In the present specification, the term "red blood cell" shall refer to a mature red blood cell throughout.) A reticulocyte corresponding to an immature red blood cell usually loses ribonucleic acid (RNA) in one to two days to become a mature red blood cell. The maturation of reticulocytes into mature red blood cells is a continuous process and several phases of reticulocytes, ranging from those that are closer to mature red blood cells than others to those that are more immature than others, exist at any one time. With reference to FIG. 9, those reticulocytes in the reticulocyte particle group that emit stronger fluorescence exhibit greater immaturity, the intensity of fluorescence weakening as the reticulocytes mature. By the time the intensity of fluorescence approaches that for mature red blood cells, the region entered is one in which reticulocytes cannot be distinguished from mature red blood cells. Accordingly, it is fair to say that the one-dimensional distribution of FIG. 9 represents a distribution of continuously maturing cells rather than a superposition of distributions of two particle groups having completely different origins. In cases such as this, it is difficult in actual practice to make an estimate about two clearly different particle groups as shown in FIG. 10 and the concept is unreasonable. Though the extrapolated curve in which the red blood cell distribution is estimated by a normal distribution is drawn in FIG. 9, the boundary between the red blood cell distribution and the reticulocytes would be an obscure one, not the distinct boundary shown.

SUMMARY OF THE INVENTION

Accordingly, an object of the present invention is to provide a realistic method of demarcating two particle groups the boundary of which is not perfectly clear physiologically or morphologically, as is the case with mature red blood cells and reticulocytes, on a plot of a one-dimensional distribution.

According to the present invention, the foregoing object is attained by providing a first method of demarcating a one-dimensional distribution in which one particle group is demarcated from another particle group by determining a threshold value thr in a plot of a one-dimensional frequency distribution having a variable X as one axis, comprising the steps of:

(a) determining a peak position $X_p$ of a distribution in the plot of the above-mentioned distribution;

(b) determining a position $X_s$, which indicates a frequency that is a predetermined percentage of the peak frequency of the distribution, on a side of the peak position $X_p$ having smaller (or larger) X values; and (c) determining the threshold value thr from the following equation:

$$thr = X_p = \alpha(X_p - X_s)$$

where $\alpha$ is a positive number.

According to the present invention, the foregoing object is attained by providing a second method of demarcating a one-dimensional distribution in which one particle group is demarcated from another particle group by determining a threshold value thr in a plot of a one-dimensional frequency distribution having a variable X as one axis, comprising the steps of:

(a) determining positions $X_s1, X_s2, \ldots X_sn$, which respectively indicate frequencies that are $\rho1, \rho2, \ldots, \rho n$ (where n is an integer of 3 or greater) of the peak frequency of a distribution, on a side of a peak position $X_p$ of the distribution in the plot of the above-mentioned distribution having smaller (or larger) X values;

(b) assuming a normal distribution on the side of the peak position $X_p$ of the distribution in the plot of the above-mentioned distribution having smaller (or larger) X values, and deriving three or more sets of relations, in which an average $\mu$ and a standard deviation $\sigma$ of the normal distribution serve as constants, from $\rho1, \rho2, \ldots, \rho n$ and $X_s1, X_s2, \ldots, X_sn$;

(c) applying the law of least squares to the three or more sets of relations and determining the average $\mu$ and the standard deviation $\sigma$ of the normal distribution; and (d) determining the threshold value thr from the following equation:

$$thr = \mu + \alpha \times \sigma$$

wherein $\alpha$ is a positive number when the normal distribution is assumed on the side of the peak position $X_p$ of the distribution having smaller X values, and $\alpha$ is a negative number when the normal distribution is assumed on the side of the peak position $X_p$ of the distribution having larger X values.

According to the present invention, the foregoing object is attained by providing a third method of demarcating a one-dimensional distribution in which one particle group is demarcated from another particle group by determining a threshold value thr in a plot of a one-dimensional frequency distribution having a variable X as one axis, comprising the steps of:

(a) determining positions $X_s1, X_s2, \ldots, X_sn$, which respectively indicate frequencies that are $\rho1, \rho2, \ldots, \rho n$ (where n is an integer of 3 or greater) of the peak frequency of a distribution, on a side of a peak position $X_p$ of the distribution in the plot of the above-mentioned distribution having smaller (or larger) X values;

(b) assuming a normal distribution on the side of the peak position $X_p$ of the distribution in the plot of the above-mentioned distribution having smaller (or larger) X values, and deriving two or more averages and two or more standard deviations of the normal distribution from $\rho1, \rho2, \ldots, \rho n$ and $X_s1, X_s2, \ldots, X_{2n}$;

(c) computing a mean value of the two or more averages and a mean value of the two or more standard deviations, and determining an average $\mu$ and a standard deviation $\sigma$ of the normal distribution; and (d) determining the threshold value thr from the following equation:

$$thr = \mu + \alpha \times \sigma$$

wherein $\alpha$ is a positive number when the normal distribution is assumed on the side of the peak position $X_p$ of the distribution having smaller X values, and $\alpha$ is a negative number when the normal distribution is assumed on the side of the peak position $X_p$ of the distribution having larger X values.

When the boundary between two particle groups is not perfectly clear physiologically or morphologically and it is physically difficult to estimate each of the distributions of the two particle groups in a region where these two distributions overlap, as is the case with mature red blood cells, and reticulocytes, use of the threshold value thr determined in the manner set forth above makes it possible to demarcate the two particle groups on a plot of a one-dimensional frequency distribution in comparatively precise fashion.

Other features and advantages of the present invention will be apparent from the following description taken in conjunction with the accompanying drawings.

BRIEF DESCRIPTION OF THE DRAWINGS

FIG. 5 and 6 are views in each of which a linear discriminant demarcating the red blood cell particle group and the reticulocyte particle group is drawn on the same two-dimensional distribution, wherein FIG. 5 shows the plot of a specimen from a healthy individual and FIG. 2 the plot of a specimen exhibiting an idiosyncrasy;

DESCRIPTION OF THE PREFERRED EMBODIMENT

A preferred embodiment of the method according to the invention will now be described with reference to the drawings.

First, a specific example of an optical system in a flow cytometer used to obtain a two-dimensional distribution and a following one-dimensional distribution in the present embodiment will be described with reference to FIG. 7.

Figure 7:
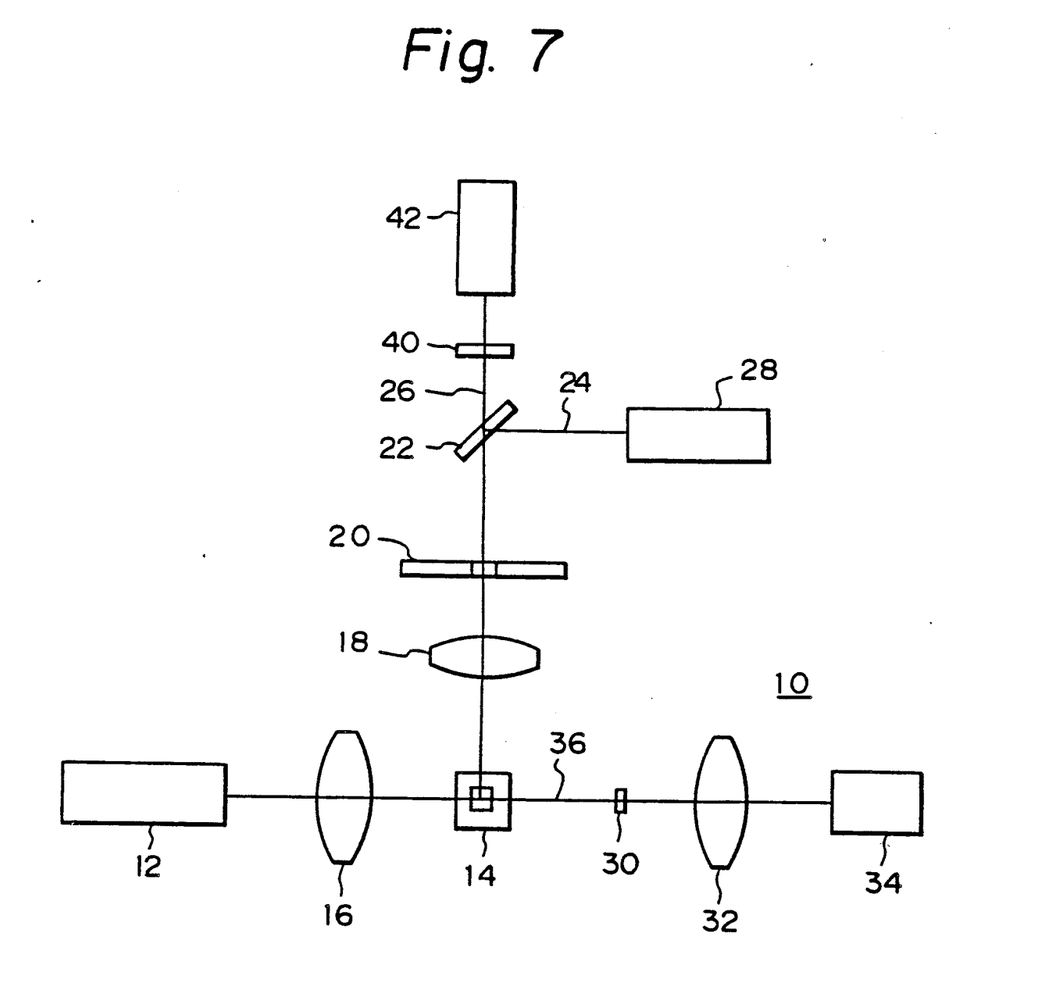
FIG. 7 is a schematic view showing a specific example of the optical system in a flow cytometer used in an embodiment of the present invention.

FIG. 7 illustrates the basic arrangement of an optical system for measuring the intensities of forward-scattered light, side-scattered light and fluorescence. The present embodiment deals with a plot of a two-dimensional distribution in which the parameters are the intensity of forward-scattered light and the intensity of fluorescence. However, if the purpose of measurement differs, it is possible to obtain a plot of a two-dimensional distribution using another combination of parameters, such as the intensity of side-scattered light and the intensity of fluorescence.

A light source used in an optical system 10 of this flow cytometer is an argon ion laser 12 having a wavelength of 488 nm and an output power of 10 mW. The light emitted by the laser 12 is converged by a cylindrical lens 16 so as to irradiate a specimen flowing through a flow cell 14. When laser beam impinges upon a particle in the specimen, the beam is scattered. If the particle has been dyed with a fluorescent dye, the irradiated particle emits fluorescence. The side-scattered light and the fluorescence are condensed by a condenser lens 18 and reach a dichroic mirror 22 upon passing through an aperture 20.

The dichroic mirror 22 reflects the side-scattered light, which is shown at numeral 24, and transmits the fluorescence, which is indicated at numeral 26. The side-scattered light reflected by the dichroic mirror 22 is measured by a photoelectron multiplier tube 28. The fluorescence 26 transmitted by the dichroic mirror 22 is measured by a photoelectron multiplier tube 42 upon passing through a color filter 40. The dichroic mirror 22 and photoelectron multiplier tube 28 can be dispensed with if the side-scattered light is not measured.

The laser beam transmitted forwardly through the flow cell 14 and light scattered forwardly along an optic axis 36 by a particle in the specimen are blocked by a beam stopper 30 and therefore do not impinge directly upon a photodiode 34. Light contained in the narrow-angle forward-scattered light that is not blocked by the beam stopper 30 is condensed by the condenser lens 32 and then received by the photodiode 34.

Figure 3:
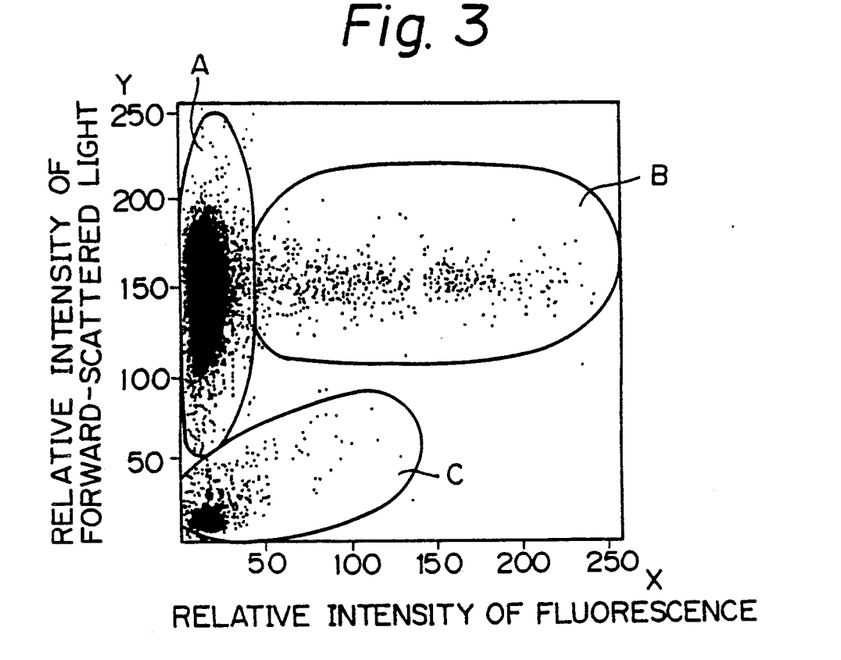
FIG. 3 is a view showing an example of the plot of a two-dimensional distribution obtained when a blood sample is dyed with auramine O and measured by a flow cytometer.

The plot of FIG. 3 is obtained when blood fluorescently dyed with the dye auramine 0 is adopted as the specimen, the speciment is passed through the flow cell 14, fluorescence and side-scattered light are measured by the above-described flow cytometer, and a two-dimensional distribution is plotted with the intensity of fluorescence and the intensity of side-scattered light serving as the two axes. Here the horizontal axis represents the relative intensity of fluorescence and the vertical axis the relative intensity of forward-scattered light. Each point in FIG. 3 corresponds to an individual particle, A represents the red blood cell particle group, B the reticulocyte particle group and C the platelet particle group. Hereinafter the vertical axis, horizontal axis and characters have the same meanings in FIG. 4 through 6 as well. The intensity of fluorescence and the intensity of side-scattered light are indicated upon being subjected to analog/digital conversion processing in which the full scale is equally divided into 256 resolution graduations. Since reticulocytes are uniquely dyed by auramine 0 and fluoresce when irradiated with laser light, the reticulocyte particle group appears in the enclosed region B. Since the red blood cells exhibit a large scattered light intensity and little fluorescence, the red blood cell particle group appears in the enclosed region A. The platelets exhibit little fluorescent intensity and little scattered light intensity and therefore appear in the enclosed region C. If the number of particles in each of these regions is counted, the number of particles in each particle group present in the specimen can be determined. In order to accomplish this, it is necessary to draw a discriminant on the plot of the two-dimensional distribution for the purpose of demarcating the particle groups. The illustrated embodiment specifically deals with a manner of drawing a discriminant which demarcates the red blood cell particle group and the reticulocyte particle group after the platelet particle group is first demarcated and excluded.

Figure 4:
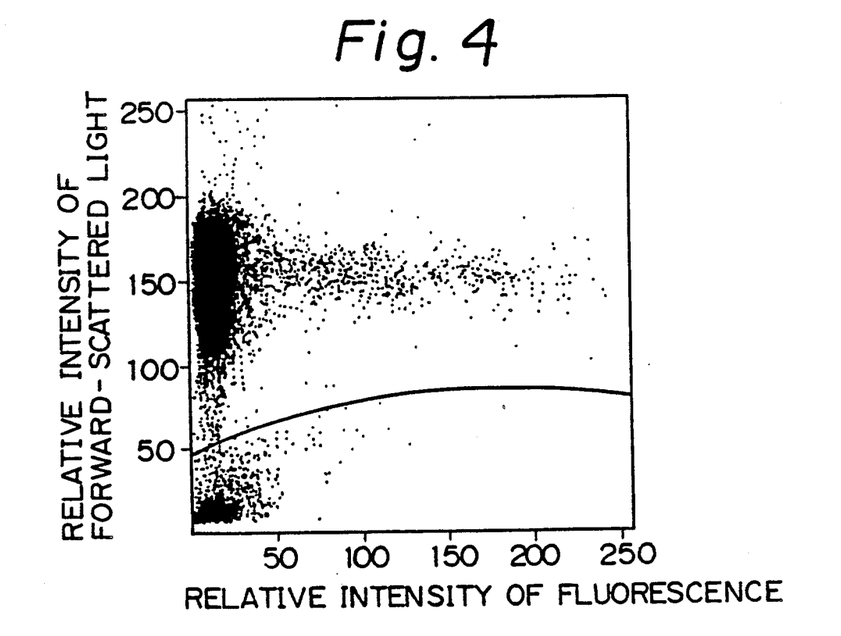
FIG. 4 is a view in which a discriminant curve demarcating a red blood cell particle group and a reticulocyte particle group from a platelet particle group is drawn on the same two dimensional distribution.

The curve plotted in FIG. 4 is a discriminant curve, which is drawn by finding a region of sparse data in the distribution, and demarcates a red blood cell particle group and a reticulocyte particle group from a platelet particle group.

Figure 1:
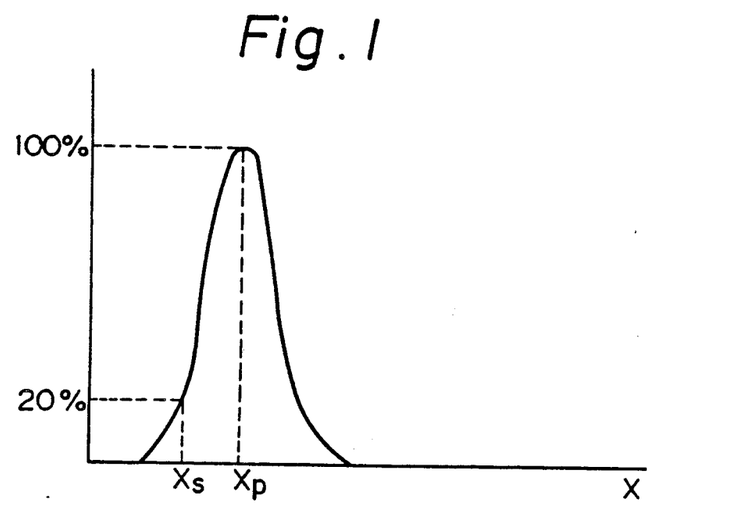
FIG. 1 is a view useful in describing a technique for determining a threshold value in a one-dimensional distribution according to a first method of the present invention.

When a one-dimensional frequency distribution having the relative intensity of fluorescence as its horizontal axis is plotted after the particle group below the discriminant curve, namely the platelet particle group, is excluded from the distribution of FIG. 1, the distribution obtained is as shown in FIG. 1. The vertical axis of FIG. 1 represents relative frequency; peak frequency is indicated as 100%. It should be noted that FIG. 1 is a conceptual view and does not precisely correspond to FIG. 4 (the same is true of FIG. 2). A comparison of FIG. 1 with the two-dimensional distribution of FIG. 4 reveals that the large mountain-shaped distribution in FIG. 1 is substantially ascribable to the red blood cell particle group, and that the reticulocyte particle group is distributed over a wide area, beginning from the foot of the mountain on its right side and extending almost the full scale of fluorescence intensity. Since the red blood cells and reticulocytes do not have a boundary which is perfectly defined physiologically or morphologically, the boundary of the red blood cell particle and reticulocyte particle distributions is essentially unclear i FIG. 1 as well, as set forth earlier. Two examples of demarcation methods for such a case will now be described.

Figure 5:
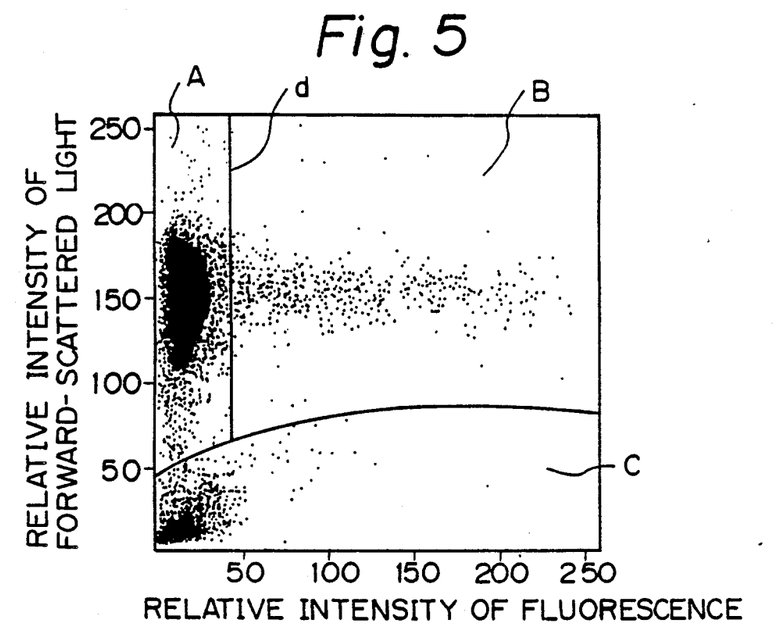
Figure 6:
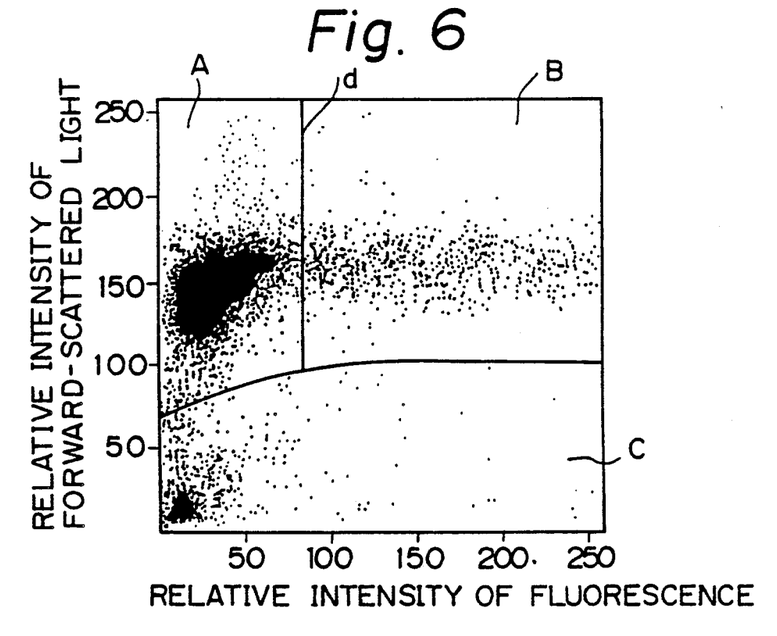

(1) Method I of Demarcating a Red Blood Cell Particle Group and a Reticulocyte Particle Group In the one-dimensional frequency distribution shown in FIG. 1, the position of the peak is found. Let this position be represented by $X_p$. Next, let $X_s$ represent a position indicating a frequency which is 20% of the peak frequency. (It is not absolutely necessary that the frequency be 20% of peak frequency; ordinarily, any frequency between 10% and 65% of peak will suffice.) A threshold value thr of fluorescent intensity between red blood cells and reticulocytes is obtained in accordance with the following equation:

$$thr = X_p + a(X_p - X_s) \quad (1)$$

where α is a positive number the numerical value of which is suitably selected based on experimentation or design. If a discriminant between the red blood cell particle group and the reticulocyte particle group is drawn using the threshold value thr found by evaluating Eq. (1) with α set at 4.25, a plot of the kind shown in FIGS. 5 and 6 is obtained. The vertically extending straight line d is the discriminant. FIG. 5 is a plot of results obtained when measuring the blood sample of a healthy individual, and FIG. 6 is a plot of results obtained when measuring a blood sample exhibiting an idiosyncrasy. Here the distribution of the red blood cell particle group exhibits a greater spread toward the right. Consequently, the position of the discriminant between the red blood cell particle group and the reticulocyte particle group is shifted farther to the right in comparison with FIG. 5. If the number of particles in area B in both figures is obtained, the reticulocyte counts in the respective specimens can be determined. Excellent correlation is obtained between the reticulocyte count determined in accordance with the present method and that determined in accordance with the visual computing method of the prior art. With the present method, the red blood cell particle group and the reticulocyte particle group are demarcated from each in case of an idiosyncratic specimen as well as a normal specimen. Trials have shown that an accurate reticulocyte count can be determined.

(2) Method II of Demarcating a Red Blood Cell Particle Group and a Reticulocyte Particle Group Reticulocytes are uniquely dyed by bonding the RNA in the cells with the dye auradene O. Since red blood cells do not possess cellular DNA, these cells are not uniquely dyed. In addition to unique dying, both the red blood cells and reticulocytes have their cell membrane protein dyed though not as strongly as in unique dying. This is referred to an non-specific dying. In terms of the one-dimensional frequency distribution of FIG. 1, it is fair to say that unique fluorescence grows stronger toward the right side of the figure whereas non-specific fluorescence dominates toward the left side. In particular, the left side of the peak can be thought of as being a region of non-specific fluorescence due entirely to mature red blood cells.

If it is assumed here that the frequency distribution of mature red blood cell non-specific fluorescent intensity conforms to a normal distribution, then the distribution curve on the left side of the peak can be thought of as completely coinciding with a normal distribution. An average $\mu$ and a standard deviation $\sigma$ of this normal distribution can be obtained by using the distribution curve on the left side of the peak. The procedure for accomplishing this will now be described.

Figure 2:
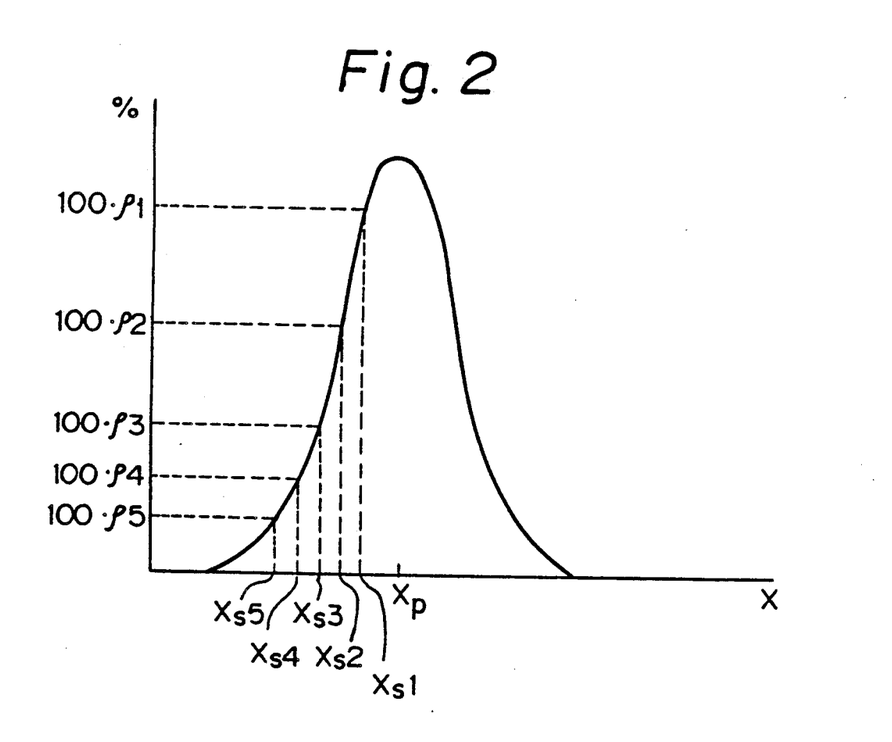
FIG. 2 is a view useful in describing techniques for determining a threshold value in a one-dimensional distribution according to second and third methods of the present invention.

FIG. 2 shows a plot of a distribution the same as that of FIG. 1 but on an enlarged scale.

A normal distribution generally is given by the following equation:

$$P(X) = \frac{1}{\sqrt{2\pi\sigma^2}} \cdot \exp\left(-\frac{(X-\mu)^2}{2\sigma^2}\right) \quad (2)$$

where X represents the value along the horizontal axis of FIG. 2.

The following equation holds when the position of a frequency which is $100\,\rho\,\%$ of the peak frequency is represented by $\mu - \epsilon\sigma$:

$$\frac{P(\mu - \epsilon\sigma)}{P(\mu)} = \rho \quad (3)$$

Solving the left side of this equation gives us $$\frac{P(\mu - \epsilon\sigma)}{P(\mu)} = \frac{\frac{1}{\sqrt{2\pi\sigma^2}} \cdot \exp\left(-\frac{\epsilon^2}{2}\right)}{\frac{1}{\sqrt{2\pi\sigma^2}}} = \exp\left(-\frac{\epsilon^2}{2}\right) \quad (4)$$

Substituting Eq. (4) into Eq. (3) and solving for $\epsilon$ gives us $$-\frac{\epsilon^2}{2} = \ln(\rho) \quad (5)$$

$$\epsilon = \sqrt{-2 \cdot \ln(\rho)}$$

Values of X on the left side of the peak where the frequency values are $100 \cdot \rho 1\%$, $100 \cdot \rho 2\%$, $100 \cdot \rho 3\%$, $100 \cdot \rho 4\%$ and $100 \cdot \rho 5\%$ of peak are determined and these X values are denoted $X_s1$, $X_s2$, $X_s3$, $X_s4$ and $X_s5$, respectively (see FIG. 2). When this is done, the following Equations (6) through (10) are established:

$$\mu - \epsilon 1 \cdot \sigma = X_s 1; \quad (6)$$

$$\epsilon 1 = \sqrt{-2 \cdot \ln(\rho 1)}$$

$$\mu - \epsilon 2 \cdot \sigma = X_s 2; \quad (7)$$

$$\epsilon 2 = \sqrt{-2 \cdot \ln(\rho 2)}$$

$$\mu - \epsilon 3 \cdot \sigma = X_s 3; \quad (8)$$

$$\epsilon 3 = \sqrt{-2 \cdot \ln(\rho 3)}$$

$$\mu - \epsilon 4 \cdot \sigma = X_s 4; \quad (9)$$

$$\epsilon 4 = \sqrt{-2 \cdot \ln(\rho 4)}$$

$$\mu - \epsilon 5 \cdot \sigma = X_s 5; \quad (10)$$

$$\epsilon 5 = \sqrt{-2 \cdot \ln(\rho 5)}$$

Letting $X_s$ and $\epsilon$ be variables, the constants $\mu$ and $\sigma$ can be obtained if the law of least squares is applied to Eqs. (6)–(10).

Alternatively, $\mu$ and $\sigma$ can be obtained as set forth hereinbelow without using the law of least squares.

Specifically, four values of $\mu$ and four values of $\sigma$ are obtained as follows from Eqs. (6)–(10):

$$\sigma 1 = (X_s 1 - X_s 5)/(\epsilon 5 - \epsilon 1)$$

$$\mu 1 = X_s 1 + \epsilon 1 \cdot \sigma 1$$

$$\sigma 2 = (X_s 2 - X_s 5)/(\epsilon 5 - \epsilon 2)$$

$$\mu 2 = X_s 2 + \epsilon 2 \cdot \sigma 2$$

$$\sigma 3 = (X_s 3 - X_s 5)/(\epsilon 5 - \epsilon 3)$$

$$\mu 3 = X_s 3 + \epsilon 3 \cdot \sigma 3$$

$$\sigma 4 = (X_s 4 - X_s 5)/(\epsilon 5 - \epsilon 4)$$

$$\mu 4 = X_s 4 + \epsilon 4 \cdot \sigma 4$$

The mean value of the four values of $\mu$ and the mean value of the four values of $\sigma$ are obtained and these are adopted as the $\mu$ and $\sigma$ of the estimated normal distribution.

Here particles having an intensity of fluorescence greater than the threshold value thr determined by the equation $$thr = \mu + \alpha \times \sigma \tag{11}$$

are treated as reticulocytes, where $\alpha$ is a positive number the numerical value of which is suitably selected by experimentation or design. If a discriminant between the red blood cell particle group and the reticulocyte particle group is drawn using the threshold value thr found by evaluating Eq. (11) with $\alpha$ set at 7.0, a plot of the kind shown in FIGS. 5 and 6 is obtained.

In this example, five points are taken on the distribution curve in order to determine $\mu$ and $\sigma$. However, the number of points can be selected appropriately. In accordance with the method of example (2), $\mu$ and $\sigma$ are found by the method of least squares or by averaging a plurality of values. This makes it possible to obtain a more accurate threshold value thr than is feasible with method of example (1).

Though the method of least squares provides a more accurate threshold value thr than the method of averaging a plurality of values, the latter method involves simpler processing. If a processing program based on the method of the present invention is incorporated in a particle analyzer, the method of averaging a plurality of values is advantageous in terms of processing speed and cost.

In accordance with the method of the present invention, it is possible to demarcate two particle groups the boundary of which is not perfectly clear physiologically or morphologically, as is the case with mature red blood cells and reticulocytes, on a plot of a one-dimensional distribution with comparatively good accuracy.

In particular, with the second and third methods of the invention, a one-dimensional distribution can be demarcated with even greater accuracy since an average and a standard deviation of a normal distribution are computed using several points on the distribution curve and a threshold value is determined which demarcates two particle groups from each other.

As many apparently widely different embodiments of the present invention can be made without departing from the spirit and scope thereof, it is to be understood that the invention is not limited to the specific embodiments thereof except as defined in the appended claims.

What is claimed is:

1. A method of demarcating a one-dimensional distribution in which a reticulocyte particle group in a blood sample is demarcated from another particle group in the sample by determining a threshold value thr in a plot of a one-dimensional frequency distribution prepared from signals indicative of fluorescence detected from individual particles during flow cytometry having a variable X as one axis, comprising the steps of:

(a) preparing a specimen for measuring by mixing a sample of blood with a fluorescent dye solution, said dye solution comprising a fluorescent dye which uniquely dyes reticulocyte particles in said blood sample;

(b) introducing an aliquot of the specimen prepared in accordance with step (a), into a flow cell of a flow cytometer, irradiating particles of said aliquot of said specimen in said flow cytometer with a light of a wavelength that excites fluorescence of said fluorescent dye, (c) measuring from said particles of said aliquot relative intensities of a fluorescence signal due to said fluorescent dye absorbed by said particles and relative intensities of a signal of scattered light from said wavelength of light;

(d) identifying from the particles of said aliquot a one-dimensional frequency distribution of particles consisting of red blood cell particles and reticulocyte particles, said one-dimensional frequency distribution identified on the basis of relative intensities of fluorescence and relative intensities of scattered light;

(e) demarcating said reticulocyte particles from said red blood cell particles by determining positions $Xs_1, Xs_2, \ldots, Xs_n$, which respectively indicate frequencies that are $p_1, p_2, \ldots p_n$ (where n is an integer of 3 or greater) of the peak frequency of a distribution, on a side of a peak position Xp of the distribution in the plot of said distribution having smaller (or larger) X values;

(f) assuming a normal distribution on the side of the peak position Xp of the distribution in the plot of said distribution having smaller (or larger) X values, and deriving three or more sets of relations, in which an average $\mu$ and a standard deviation $\sigma$ of the normal distribution serve as constants, from $p_1, p_2, \ldots p_n$ and $Xs_1, Xs_2, \ldots, Xs_n$;

(g) applying the law of least squares to said three or more sets of relations and determining the average $\mu$ and the standard deviation $\sigma$ of the normal distribution; and (h) determining the threshold value thr from the following equation:

$$thr = \mu + \alpha \times \sigma$$

where in $\alpha$ is a positive number when the normal distribution is assumed on the side of the peak position Xp of the distribution having smaller X values, and $\alpha$ is a negative number when the normal distribution is assumed on the side of the peak position Xp of the distribution having larger X values.

2. A method of demarcating a one-dimensional distribution in which a reticulocyte particle group in a blood sample is demarcated from another particle group in the sample by determining a threshold value thr in a plot of a one-dimensional frequency distribution prepared from signals indicative of fluorescence detected from individual particles during flow cytometry having a variable X as one axis, comprising the steps of:

(a) preparing a specimen for measuring by mixing a sample of blood with a fluorescent dye solution, said dye solution comprising a fluorescent dye which uniquely dyes reticulocyte particles in said blood sample;

(b) introducing an aliquot of the specimen prepared in accordance with step (a), into a flow cell of a flow cytometer irradiating particles of said aliquot of said specimen in said flow cytometer with a light of a wavelength that excites fluorescence of said fluorescent dye, (c) measuring from said particles of said aliquot relative intensities of a fluorescence signal due to said fluorescent dye absorbed by said particles and relative intensities of a signal of scattered light from said wavelength of light;

(d) identifying from the particles of said aliquot a one-dimensional frequency distribution of particles consisting of red blood cell particles and reticulocyte particles, said one-dimensional frequency distribution identified on the basis of relative intensities of fluorescence and relative intensities of scattered light;

(e) demarcating said reticulocyte particles from said red blood cell particles by determining positions $Xs_1, Xs_2, \ldots, Xs_n$, which respectively indicate frequencies that are $p_1, p_2, \ldots, p_n$ (where n is an integer of 3 or greater) of the peak frequency of a distribution, on a side of a peak position Xp of the distribution in the plot of said distribution having smaller (or larger) X values;

(f) assuming a normal distribution on the side of the peak position Xp of the distribution in the plot of said distribution having smaller (or larger) X values, and obtaining two or more averages and two or more standard deviations of the normal distribution from $p_1, p_2, \ldots, p_n$ and $Xs_1, Xs_2, \ldots Xs_n$;

(g) computing a mean value of said two or more averages and a mean value of said two or more standard deviations, and determining an average $\mu$ and a standard deviation $\sigma$ of the normal distribution; and (h) determining the threshold value thr from the following equation:

$$thr = \mu + \alpha \times \sigma$$

wherein $\alpha$ is a positive number when the normal distribution is assumed on the side of the peak position Xp of the distribution having smaller X values, and $\alpha$ is a negative number when the normal distribution is assumed on the side of the peak position Xp of the distribution having larger X values.

* * * * *

UNITED STATES PATENT AND TRADEMARK OFFICE
CERTIFICATE OF CORRECTION

PATENT NO.   : 5,117,357
DATED        : May 26, 1992
INVENTOR(S)  : Takanobu Inoue It is certified that error appears in the above-identified patent and that said Letters Patent is hereby corrected as shown below:

Column 1, line 52, change "fluorescense" to --fluorescence--

Column 3, line 17, change "thr = $X_p$ = $\alpha(X_p - X_s)$" to --thr = $X_p + \alpha(X_p - X_s)$--.

Column 3, line 27, change "$X_s2, ...X_sn$" to --$X_s2, ..., X_sn$--.

Column 6, line 50, after "unclear" change "i" to --in--.

Signed and Sealed this

Twenty-eighth Day of September, 1993

Attest:

BRUCE LEHMAN

*Attesting Officer*     *Commissioner of Patents and Trademarks*